(12) United States Patent
Dong et al.

(10) Patent No.: US 12,239,309 B2
(45) Date of Patent: Mar. 4, 2025

(54) ALL SUTURE ANCHOR AND ANCHOR PULLING-AND-FORMING KIT

(71) Applicant: Star Sports Medicine Co., Ltd., Beijing (CN)

(72) Inventors: Wenxing Dong, Beijing (CN); Jichen Yin, Beijing (CN)

(73) Assignee: Star Sports Medicine Co., Ltd., Beijing (CN)

(*) Notice: Subject to any disclaimer, the term of this patent is extended or adjusted under 35 U.S.C. 154(b) by 407 days.

(21) Appl. No.: 17/693,135

(22) Filed: Mar. 11, 2022

(65) Prior Publication Data
US 2022/0211363 A1 Jul. 7, 2022

Related U.S. Application Data

(63) Continuation of application No. PCT/CN2021/141544, filed on Dec. 27, 2021.

(30) Foreign Application Priority Data

Jan. 27, 2021 (CN) .......................... 202110108680.9

(51) Int. Cl.
*A61B 17/04* (2006.01)

(52) U.S. Cl.
CPC .. *A61B 17/0401* (2013.01); *A61B 2017/0414* (2013.01); *A61B 2017/042* (2013.01); *A61B 2017/0445* (2013.01)

(58) Field of Classification Search
CPC ........ A61B 17/0401; A61B 2017/0414; A61B 2017/042; A61B 2017/0445
See application file for complete search history.

(56) References Cited

U.S. PATENT DOCUMENTS

| 5,269,809 A | 12/1993 | Hayhurst |
| 2007/0185532 A1 | 8/2007 | Stone et al. |
| 2008/0065114 A1 | 3/2008 | Stone |

(Continued)

FOREIGN PATENT DOCUMENTS

| CN | 105163673 A | 12/2015 |
| CN | 106028959 A | 10/2016 |

(Continued)

OTHER PUBLICATIONS

Notification to Grant Patent Right for Invention dated Apr. 5, 2024 for Chinese Application No. 202110108680.9.

(Continued)

*Primary Examiner* — Tan-Uyen T Ho
*Assistant Examiner* — Cherie M Poland

(57) ABSTRACT

The present application provides an all suture anchor, and relates to the technical field of medical devices. The all suture anchor includes a suture anchor body and a pulling suture. The suture anchor body is in a shape of cylinder, a first end port and a second end port are respectively formed at two ends of the suture anchor body in an axis direction of itself, and a first through hole is formed at a side wall of the suture anchor body close to the first end port; a fixed end of the pulling suture enters into the suture anchor body from the first end port and passes out from the first through hole, and the fixed end of the pulling suture is fixedly arranged on the suture anchor body.

5 Claims, 3 Drawing Sheets

(56) References Cited

U.S. PATENT DOCUMENTS

| | | |
|---|---|---|
| 2012/0197271 A1 | 8/2012 | Astorino et al. |
| 2013/0123810 A1 | 5/2013 | Brown |
| 2016/0058436 A1* | 3/2016 | Stone ................. A61B 17/0401 606/232 |
| 2016/0174963 A1* | 6/2016 | Oren .................. A61B 17/0401 606/232 |
| 2016/0220243 A1 | 8/2016 | Astorino |
| 2020/0029955 A1 | 1/2020 | Stone |

FOREIGN PATENT DOCUMENTS

| | | | |
|---|---|---|---|
| CN | 110215248 A | 9/2019 | |
| CN | 110353747 A | 10/2019 | |
| CN | 210811258 U | 6/2020 | |
| CN | 210931753 U | 7/2020 | |
| CN | 211560209 U | 9/2020 | |
| CN | 112754559 A | 5/2021 | |
| CN | 215228014 U | 12/2021 | |
| WO | 2020/252372 A1 | 12/2020 | |
| WO | WO-2022161065 A1 * | 8/2022 | ......... A61B 17/0401 |
| WO | 2023/081171 A1 | 5/2023 | |

OTHER PUBLICATIONS

The Office Action for European Patent Application No. 21859377.0, dated Jul. 17, 2023.
The Extended European Search Report for European Patent Application No. 21859377.0, dated Nov. 24, 2022.
International Search Report for International Application No. PCT/CN2021/141544, dated Mar. 29, 2022.

* cited by examiner

ALL SUTURE ANCHOR AND ANCHOR PULLING-AND-FORMING KIT

CROSS REFERENCE TO RELATED APPLICATION

The present application is a continuation of International Application No. PCT/CN2021/141544, filed on Dec. 27, 2021, which claims priority to Chinese Patent Application No. 202110108680.9, filed on Jan. 27, 2021, titled with "ALL SUTURE ANCHOR AND ANCHOR PULLING-AND-FORMING KIT", both of which are hereby incorporated by reference in their entireties.

TECHNICAL FIELD

The present application relates to the technical field of medical devices, and in particular an all suture anchor and an anchor pulling-and-forming kit.

BACKGROUND

A suture anchor is widely used in medicine for the connection and fixation of human soft tissue and bone tissue. The material of the anchor may be a metal, a polyetheretherketone (PEEK), an absorbable material, and a material that is homogenous to suture. The last type of suture anchor is called an all suture anchor.

An anchor body of the above-mentioned all suture anchor is generally directly penetrated by a suture thread, after placing the suture thread in the anchor body, the anchor body is folded in half, and then implanted into the cancellous bone with an inserter, and finally two ends of the suture thread are pulled to lock a fixed point. In clinical applications, for the all suture anchor with such structures, the anchor body often cannot be deformed or the deformation amount is very small, and it is difficult to achieve tangential expansion of the anchor body and then lock the anchor body in a bone canal hole.

SUMMARY

The object of the present application is to provide an all suture anchor and an anchor pulling-and-forming kit, so that it can be helpful to solve the above technical problems.

In one aspect, embodiments of the present application provides the all suture anchor, including a suture anchor body and a pulling suture. Herein, the suture anchor body is in a shape of cylinder, a first end port and a second end port are respectively formed at two ends of the suture anchor body in an axis direction of itself, and a first through hole is formed at a side wall of the suture anchor body close to the first end port; a fixed end of the pulling suture enters into the suture anchor body from the first end port and passes out from the first through hole, and the fixed end of the pulling suture is fixedly arranged on the suture anchor body.

When the above-mentioned all suture anchor is used, an inserter is implanted into the cancellous bone in advance, and the pulling suture passes through the first through hole instead of being fixed with the first through hole, and the fixed end of the pulling suture extends and fixed on the suture anchor body, therefore, when the pulling suture is pulled, the suture anchor body is squeezed and bent in the cancellous bone, and a bent part is not squeezed by the inserter to form a crease, so the suture anchor body expands greatly in a tangential direction of a pulling force, thereby ensuring that the anchor body can be fixed in the cancellous bone.

According to the embodiments of the aspect of the present application, the fixed end of the pulling suture is fixedly arranged on an outer wall of a middle section of the suture anchor body. The technical effect of the structure is as follows: the fixed end of the pulling suture is fixed on the outer wall of the middle section of the suture anchor body, which is easy to manufacture and form, and the pulling deformation is also simple and quick. After the pulling suture is pulled, the suture anchor body is bent into three curved sections, and finally forms a Y-shaped anchor segment, so that the tangential expansion of the suture anchor body is greater; the Y-shaped anchor segment will firmly clamp a bone canal, providing a strong anti-pullout resistance for the entire all suture anchor, so the fixation effect in the cancellous bone is better. Since the structure of the Y-shaped anchor segment enables the anchor body to cut into a surrounding bone tissue at any angle, so as to achieve the purpose of improving fixation.

According to the embodiments of the aspect of the present application, the fixed end of the pulling suture is fixedly arranged on the outer wall of the suture anchor body close to the second end port. The technical effect of the structure is as follows: although the suture anchor body has only one bend after the pulling suture is pulled, the suture anchor body is not squeezed into a flat sheet-like structure after bending, thus, it can still ensure the locking and fixing effect of the pulling suture.

According to the embodiments of the aspect of the present application, a side wall of the middle section of the suture anchor body further provided with a second through hole, and the fixed end of the pulling suture enters into an inner cavity of the suture anchor body from the second through hole and is fixed on an inner wall of the suture anchor body. The technical effect of the structure is as follows: the second through hole is arranged at the side wall of the middle section of the suture anchor body, which can also form three curved sections after the pulling suture is pulled, and finally form a Y-shaped anchor segment, so that the tangential expansion size of the suture anchor body is larger; the Y-shaped anchor segment will firmly clamp the bone canal, providing the strong anti-pullout resistance for the all suture anchor, and the above-mentioned Y-shaped anchor segment structure enables the anchor body to cut into the surrounding bone tissue at any angle, so as to achieve the purpose of improving fixation. In addition, because the fixed end of the pulling suture enters into an interior of the suture anchor body to fix, pulling and forming the pulling suture can be more effective and convenient.

According to the embodiments of the aspect of the present application, the side wall of the middle section of the suture anchor body is further provided with the second through hole, and the fixed end of the pulling suture enters into an inner cavity of the suture anchor body from the second through hole and is fixed at the second end port. The technical effect of the structure is as follows: after entering into the anchor body from the second through hole, the fixed end of the pulling suture continues to extend to the second end port and is fixed at the second end port. Optionally, in order to make the connection between the fixed end of the pulling suture and the suture anchor body more stable, the second end port of the suture anchor body can also be blocked, and the pulling suture is wrapped around the second end port to achieve the fixed connection.

According to the embodiments of the aspect of the present application, the number of the pulling sutures is at least two. The technical effect of the structure is as follows: a plurality of pulling sutures can improve the reliability of suture threads, and prevent one of the pulling sutures from breaking, failing or being loosely connected due to instability.

Further, the pulling suture includes a plurality of suture threads, and the plurality of suture threads are wound to form the pulling suture. The technical effect of the structure is as follows: the pulling suture can be formed by spirally winding the plurality of suture threads, so that the payload of the pulling suture can be greatly improved.

According to the embodiments of the aspect of the present application, the suture anchor body is formed and woven from a plurality of suture threads. The technical effect of the structure is as follows: according to the diameter requirement of the suture anchor body, the plurality of suture threads can be used for weaving, which can increase the expansion size of the suture anchor body in the tangential direction while meet the size requirement of the suture anchor body.

According to the embodiments of the aspect of the present application, the suture anchor body is formed and woven by a diamond-shaped weaving process. The technical effect of the structure is as follows: the diamond-shaped weaving process is used in the weaving and textile industries; as the name suggests, the diamond-shaped weaving process is to weave multiple strands of single threads at an acute angle to one another to form a cloth, and the suture threads that cross one another in the cloth are not in an usual criss-cross pattern. Thus, when the suture anchor body is pulled and deformed, the deformation amount of the suture anchor body is larger than that of the ordinary crisscross cloth, so the suture anchor body has a better fixing effect the cancellous bone.

In another aspect, the embodiments of the present application further provides an anchor pulling-and-forming kit, including a packing case, an inserter and the all suture anchor as described above; each of the inserter and the all suture anchor is located in the packing case.

The present application has at least the following beneficial effects:

The all suture anchor and the anchor pulling-and-forming kit of the present application adopt the structure in which a part of the pulling suture is located in an inner cavity of the suture anchor body, and the other part is located in a periphery of the suture anchor body, so that when the pulling suture is pulled, it can squeeze the suture anchor body to bend itself to form a blocking structure with a large amount of tangential expansion and deformation, which can greatly improve the fixing performance of the suture anchor body in the cancellous bone.

BRIEF DESCRIPTION OF THE DRAWINGS

The features, advantages and technical effects of exemplary embodiments of the present application will be described below with reference to the drawings, which are not drawn to actual scale.

Figure 1:
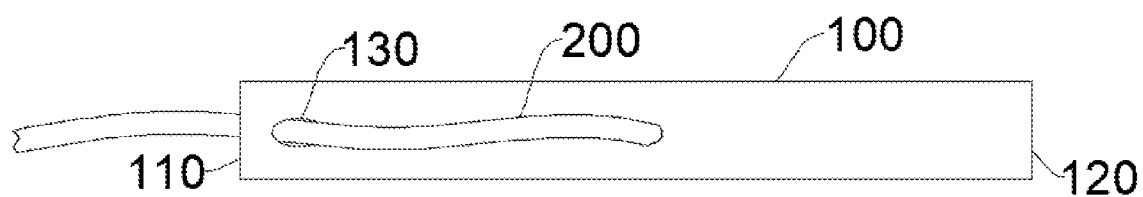
FIG. 1 shows a schematic view of an outline structure of an all suture anchor according to a first embodiment of the present application.

Reference numbers: 100—suture anchor body; 110—first end port; 120—second end port; 130—first through hole; 140—second through hole; 200—pulling suture; 300—packing case; 400—inserter.

DETAILED DESCRIPTION

Features and exemplary embodiments of various aspects of the present application are described in detail below. In the following detailed description, numerous specific details are set forth in order to provide a thorough understanding of the present application. However, it will be apparent to those skilled in the art that the present application may be practiced without some of these specific details. The following description of the embodiments is merely to provide a better understanding of the present application by illustrating examples of the present application. In the drawings and the following description, at least some well-known structures and techniques are not shown in order to avoid unnecessarily obscuring the present application; and dimensions of some structures may be exaggerated for clarity. Furthermore, the features, structures or characteristics described below may be combined in any suitable manner in one or more embodiments.

For a better understanding of the present application, an all suture anchor and an anchor pulling-and-forming kit provided by the embodiments of the present application will be described in detail below with reference to FIGS. 1 to 10.

First Embodiment

Figure 2:
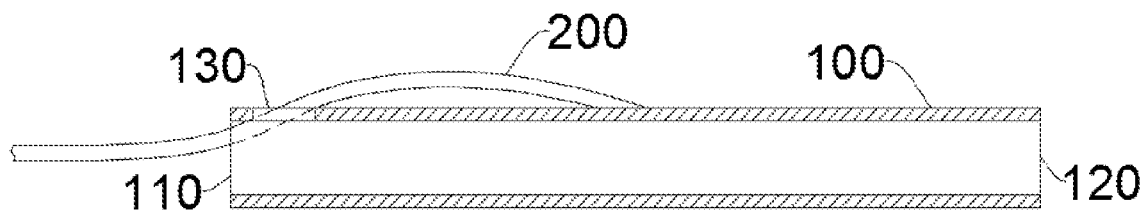
FIG. 2 shows a schematic view of an internal structure of an all suture anchor according to a first embodiment of the present application.

FIG. 1 shows a schematic view of an outline structure of the all suture anchor according to the first embodiment of the present application; FIG. 2 shows a schematic view of an internal structure of the all suture anchor according to the first embodiment of the present application. Referring to FIG. 1 and FIG. 2, the embodiment provides the all suture anchor, including a suture anchor body 100 and a pulling suture 200; the suture anchor body 100 is in a shape of cylinder, a first end port 110 and a second end port 120 are respectively formed at two ends of the suture anchor body 100 in an axis direction of itself, and a first through hole 130 is formed at a side wall of the suture anchor body 100 close to the first end port 110; a fixed end of the pulling suture 200 enters into the suture anchor body 100 from the first end port 110 and passes out from the first through hole 130, and the fixed end of the pulling suture 200 is fixedly arranged on the suture anchor body 100.

In some embodiments of the present application, as shown in FIG. 1 and FIG. 2, the fixed end of the pulling suture 200 is fixedly arranged on an outer wall of a middle section of the suture anchor body 100.

In the above structure, the fixed end of the pulling suture 200 is fixed on the outer wall of the middle section of the suture anchor body 100, which is easy to manufacture and form, and the pulling deformation is also simple and quick. After the pulling suture 200 is pulled, the suture anchor body 100 can be bent into three curved sections, and finally forms a Y-shaped anchor segment, so that the tangential expansion of the suture anchor body is greater; the Y-shaped anchor segment will firmly clamp a bone canal, providing a strong anti-pullout resistance for the entire all suture anchor, so the fixation effect in the cancellous bone is better. In addition, since the structure of the Y-shaped anchor segment enables the anchor body to cut into a surrounding bone tissue at any angle, so as to achieve the purpose of improving fixation.

A working principle and operation method of the above-mentioned all suture anchor are as follows:

When the above-mentioned all suture anchor is used, an inserter 400 is implanted into the cancellous bone in advance, and the pulling suture 200 passes through the first through hole 130 instead of being fixed with the first through hole 130, and the fixed end of the pulling suture 200 extends and fixed on the suture anchor body 100, therefore, when the pulling suture 200 is pulled, the suture anchor body 100 is squeezed and bent in the cancellous bone, and a bent part is not squeezed by the inserter 400 to form a crease, so the suture anchor body 100 expands greatly in a tangential direction of a pulling force, thereby ensuring that the anchor body can be fixed in the cancellous bone.

Second Embodiment

Figure 3:
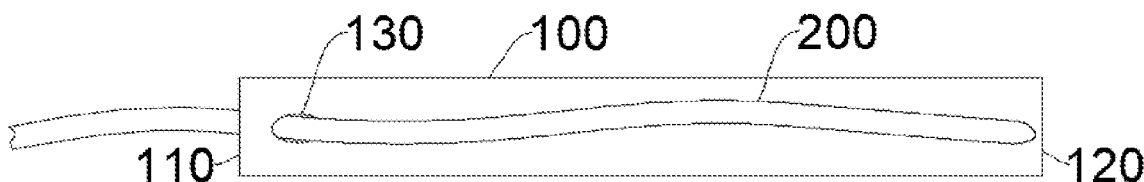
FIG. 3 shows a schematic view of an outline structure of an all suture anchor according to a second embodiment of the present application.
Figure 4:
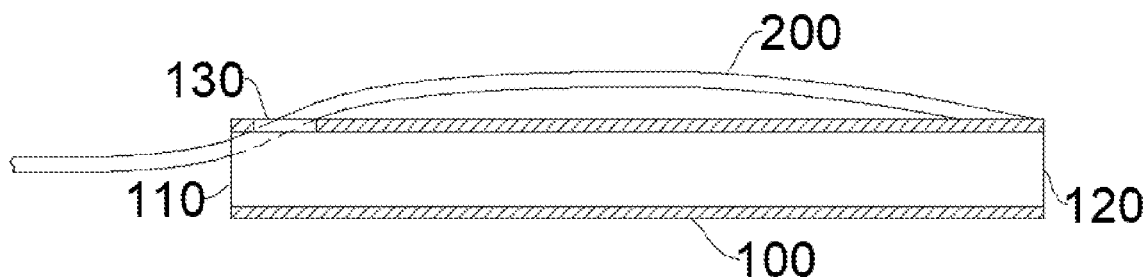
FIG. 4 shows a schematic view of an internal structure of an all suture anchor according to a second embodiment of the present application.

FIG. 3 shows a schematic view of an outline structure of the all suture anchor according to the second embodiment of the present application; FIG. 4 shows a schematic view of an internal structure of the all suture anchor according to the second embodiment of the present application. Referring to FIG. 3 and FIG. 4, this embodiment provides the all suture anchor, which is substantially the same as the all suture anchor of the first embodiment. The difference between the two all suture anchor is that in the all suture anchor of this embodiment, the fixed end of the pulling suture 200 is fixedly arranged on the outer wall of the suture anchor body 100 close to the second end port 120.

In the above structure, although the suture anchor body 100 has only one bend after the pulling suture 200 is pulled, the suture anchor body 100 is not squeezed into a flat sheet-like structure after bending, thus, it can still ensure the locking and fixing effect of the pulling suture.

Third Embodiment

Figure 5:
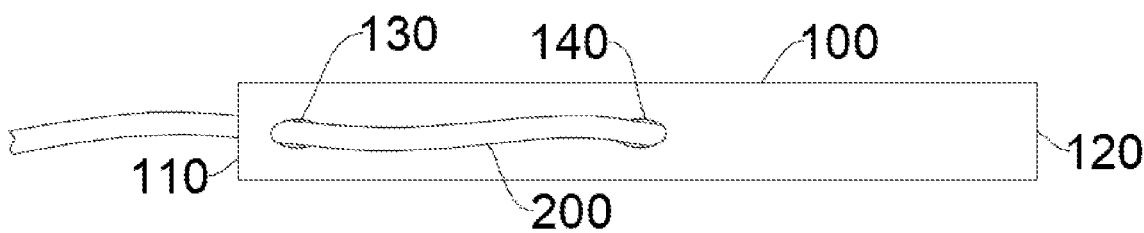
FIG. 5 shows a schematic view of an outline structure of an all suture anchor according to a third embodiment of the present application.
Figure 6:
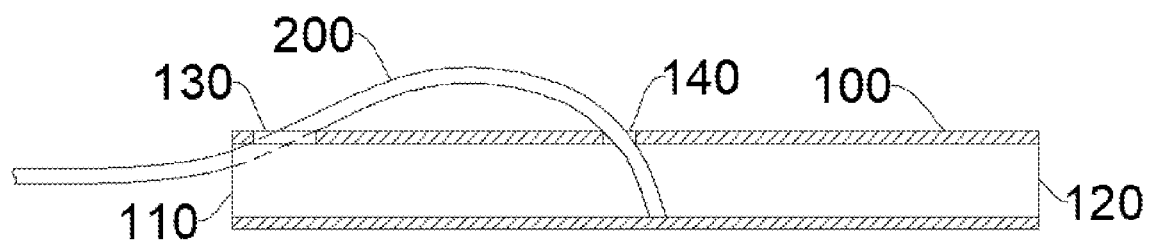
FIG. 6 shows a schematic view of an internal structure of an all suture anchor according to a third embodiment of the present application.

FIG. 5 shows a schematic view of an outline structure of the all suture anchor according to the third embodiment of the present application; FIG. 6 shows a schematic view of an internal structure of the all suture anchor according to the third embodiment of the present application. Referring to FIG. 5 and FIG. 6, this embodiment provides the all suture anchor, which is substantially the same as the all suture anchor of the first embodiment or the second embodiment. The difference between the two all suture anchor is that in the all suture anchor of this embodiment, a side wall of the middle section of the suture anchor body 100 further provided with a second through hole 140, and the fixed end of the pulling suture 200 enters into an inner cavity of the suture anchor body 100 from the second through hole 140 and is fixed on an inner wall of the suture anchor body 100.

In the above structure, the second through hole 140 is arranged at the side wall of the middle section of the suture anchor body 100, which can also form three curved sections after the pulling suture 200 is pulled, and finally form the Y-shaped anchor segment, so that the tangential expansion size of the suture anchor body is larger; the Y-shaped anchor segment will firmly clamp the bone canal, providing the strong anti-pullout resistance for the all suture anchor, and the above-mentioned Y-shaped anchor segment structure enables the anchor body to cut into the surrounding bone tissue at any angle, so as to achieve the purpose of improving fixation. In addition, because the fixed end of the pulling suture 200 enters into an interior of the suture anchor body 100 to fix, pulling and forming the pulling suture 200 can be more effective and convenient.

Fourth Embodiment

Figure 7:
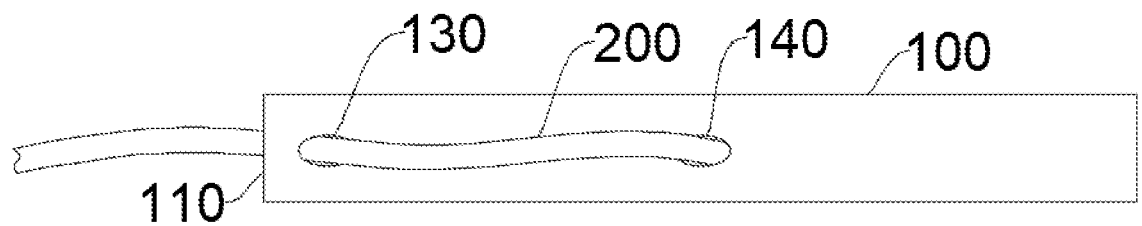
FIG. 7 shows a schematic view of an outline structure of an all suture anchor according to a fourth embodiment of the present application.
Figure 8:
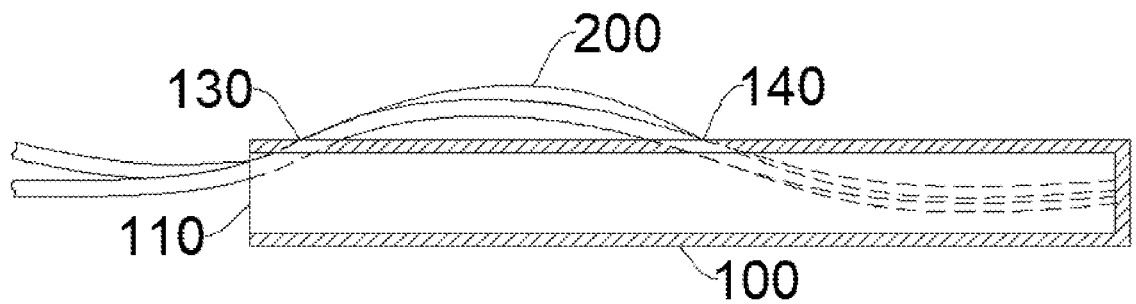
FIG. 8 shows a schematic view of an internal structure of an all suture anchor according to a fourth embodiment of the present application.

FIG. 7 shows a schematic view of an outline structure of the all suture anchor according to a fourth embodiment of the present application; FIG. 8 shows a schematic view of an internal structure of the all suture anchor according to a fourth embodiment of the present application. Referring to FIG. 7 and FIG. 8, this embodiment provides the all suture anchor, which is substantially the same as the all suture anchor of the first embodiment, the second embodiment or the third embodiment. The difference between the two all suture anchor is that in the all suture anchor of this embodiment, a side wall of a middle section of the suture anchor body 100 is further provided with a second through hole 140, and the fixed end of the pulling suture 200 enters into an inner cavity of the suture anchor body 100 from the second through hole 140 and is fixed at the second end port 120.

In the above structure, after entering into the anchor body 100 from the second through hole 140, the fixed end of the pulling suture 200 continues to extend to the second end port 120 and is fixed at the second end port 120. Particularly, in order to make the connection between the fixed end of the pulling suture 200 and the suture anchor body 100 more stable, the second end port 120 of the suture anchor body 100 can also be blocked, and the pulling suture 200 is wrapped around the second end port 120 to achieve the fixed connection.

Based on any one of the above-mentioned embodiments, optionally, as shown in FIG. 8, the number of the pulling sutures 200 is at least two. Optionally, the number can be chosen to be 2, 4, 6 or even more. At this time, a plurality of pulling sutures 200 can improve the reliability of suture threads, and prevent one of the pulling sutures 200 from breaking, failing or being loosely connected due to instability.

Based on any one of the above-mentioned embodiments, optionally, the pulling suture 200 includes a plurality of suture threads, and the plurality of suture threads are wound to form the pulling suture 200. The pulling suture 200 can be formed by spirally winding the plurality of suture threads, so that the payload of the pulling suture 200 can be greatly improved.

Figure 10:
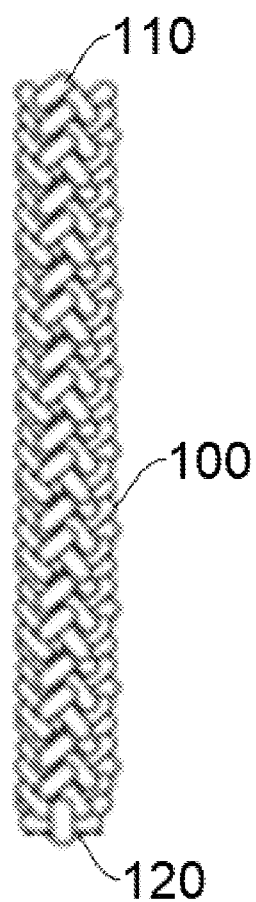
FIG. 10 shows a structural schematic view of a suture anchor body in an all suture anchor provided by the present application.

FIG. 10 shows a structural schematic view of the suture anchor body 100 in the all suture anchor provided by the present application. Based on any one of the above-mentioned embodiments, optionally, as shown in FIG. 10, the suture anchor body 100 is formed and woven from the plurality of suture threads. In addition, the suture anchor body 100 is formed and woven by a diamond-shaped weaving process. Herein, the diamond-shaped weaving process enables the suture anchor body 100 to be greatly deformed under the pulling action of the pulling suture 200 and improve density and stiffness of its own, so that the suture anchor body 100 can be securely fixed in the bone canal.

The number of suture threads can be any even number, such as 4 strands, 6 strands, 8 strands, etc. According to the diameter requirement of the suture anchor body 100, the plurality of suture threads can be used for weaving, which can increase the expansion size of the suture anchor body 100 in the tangential direction while meet the size requirement of the suture anchor body.

Specifically, in the diamond-shaped weaving process, several strands of suture threads are stacked and woven in a diamond shape around an axis to form a "hollow weaving tube" with obvious diamond-shaped grain lines. The pulling suture 200 can be fixed at any point of the suture anchor body 100, and this structure can be deformed by pulling at any point, so that the deformation action is reliable, the forming rate is extremely high, and the weaving process is simple and low-cost.

The suture threads in the diamond-shaped weaving process are stacked at a specific angle around the center of the anchor; after pulled, the suture threads that are overlapped with one another slide at a designed pressure angle and gather axially; an axial volume can be converted to a tangential volume, and an elongated cylinder is deformed into a stubby mass with a diameter larger than a diameter of the bone canal for anchoring and fixing in the bone. However, the traditional weaving method of the common anchor in the related art cannot produce the effect of tangential expansion and deformation, and the anchor can only be fixed by the interference fit during insertion, the contact pressure of the anchor will be greatly reduced at the moment when the inserter 400 is pulled out, and the safety and reliability in a long-term using cannot be guaranteed.

Fifth Embodiment

Figure 9:
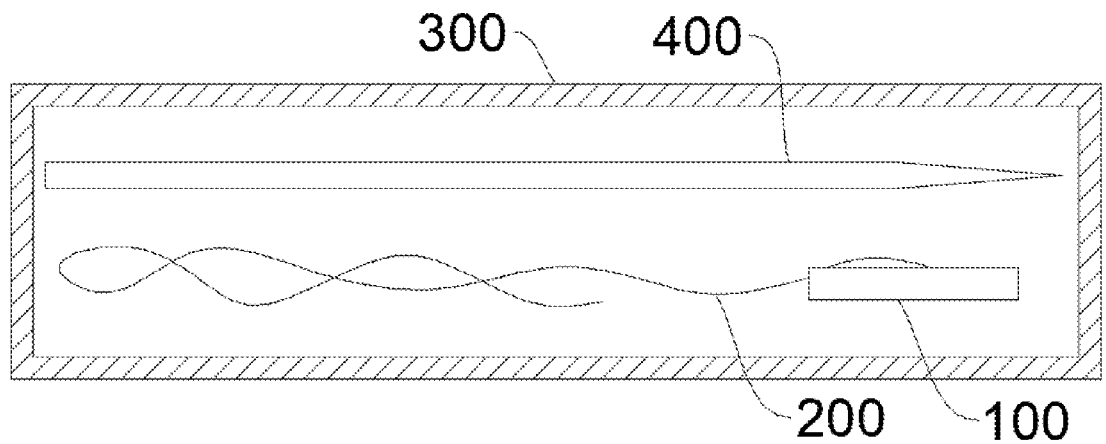
FIG. 9 shows a structural schematic view of an anchor pulling-and-forming kit according to a fifth embodiment of the present application.

FIG. 9 shows a structural schematic view of an anchor pulling-and-forming kit according to a fifth embodiment of the present application. As shown in FIG. 9, the embodiment provides the anchor pulling-and-forming kit including a packing case 300, an inserter 400 and the all suture anchor according to any one of the above-mentioned embodiments, and each of the inserter 400 and the all suture anchor is located in the packing case 300.

At this time, the inserter 400 can be used to fold the suture anchor body 100 in half into the bone canal, then the inserter 400 can be taken out, and finally the pulling suture 200 can be pulled to fix the suture threads in the bone canal.

Those skilled in the art should understand that the above-mentioned embodiments are all illustrative and not restrictive. Different technical features appearing in different embodiments can be combined to achieve beneficial effects. Those skilled in the art should be able to understand and implement other variant embodiments of the disclosed embodiments on the basis of studying the drawings, the description and the claims. In the claims, the term "comprising" does not exclude other means or steps; items are intended to include one (kind) or more (kinds) of items when they are not modified with a quantifier, and can be used interchangeably with "one (kind) or more (kinds) of items"; the terms "first", "second" are used to designate names and not to indicate any particular order. Any reference numbers in the claims shall not be construed as limiting the scope. The functions of several parts presented in the claims can be implemented by a single hardware or software module. The mere presence of certain technical features in different dependent claims does not imply that these features cannot be combined to advantage.

What is claimed is:

1. An all suture anchor, comprising
a suture anchor body, wherein the suture anchor body is in a shape of cylinder, a first end port and a second end port are respectively formed at two ends of the suture anchor body in an axis direction of itself, and a first through hole is formed at a side wall of the suture anchor body close to the first end port; and
a pulling suture, wherein a fixed end of the pulling suture enters into the suture anchor body from the first end port and passes out from the first through hole, and the fixed end of the pulling suture is fixedly arranged on the suture anchor body;
wherein a side wall of a middle section of the suture anchor body is further provided with a second through hole disposed on a same side of the axis of the suture anchor body as the first through hole, and the fixed end of the pulling suture enters into an inner cavity of the suture anchor body from the second through hole and is fixed on an inner wall of the suture anchor body; and
wherein the suture anchor body is configured to form three curved sections that form a Y-shaped anchor segment after the pulling suture is pulled.

2. The all suture anchor according to claim 1, wherein the number of the pulling sutures (200) is at least two.

3. The all suture anchor according to claim 1, wherein the pulling suture comprises a plurality of suture threads, and the plurality of suture threads are wound to form the pulling suture.

4. The all suture anchor according to claim 1, wherein the suture anchor body is formed and woven from a plurality of suture threads.

5. An anchor pulling-and-forming kit, comprising a packing case, an inserter and the all suture anchor according to claim 1, wherein each of the inserter and the all suture anchor is located in the packing case.

* * * * *